US012752363B2

(12) United States Patent
Huh et al.

(10) Patent No.: US 12,752,363 B2
(45) Date of Patent: Oct. 6, 2026

(54) WELDING INFORMATION PROVIDING APPARATUS

(71) Applicant: OTOS WING CO., LTD., Seoul (KR)

(72) Inventors: Moon Young Huh, Seoul (KR); Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 725 days.

(21) Appl. No.: 18/307,311

(22) Filed: Apr. 26, 2023

(65) Prior Publication Data

US 2023/0364719 A1 Nov. 16, 2023

(30) Foreign Application Priority Data

May 10, 2022 (KR) ........................ 10-2022-0057405

(51) Int. Cl.
*B23K 9/32* (2006.01)
*A61F 9/06* (2006.01)
*B23K 37/006* (2025.01)

(52) U.S. Cl.
CPC .............. *B23K 9/322* (2013.01); *A61F 9/064* (2013.01); *B23K 37/006* (2013.01)

(58) Field of Classification Search
CPC ............ A61F 9/06; A61F 9/064; B23K 9/322
See application file for complete search history.

(56) References Cited

U.S. PATENT DOCUMENTS 10,701,270 B1 * 6/2020 LaFlech ................. H04N 23/63
2010/0223706 A1 * 9/2010 Becker ................... G10K 11/18 381/151
2011/0083241 A1 * 4/2011 Cole ......................... A61F 9/06 2/8.2
2012/0291172 A1 * 11/2012 Wills ..................... H04N 23/20 219/136
2015/0026872 A1 * 1/2015 Giroux Bernier ....... A42B 3/04 29/428
2022/0095736 A1 3/2022 Henshaw
2023/0117584 A1 * 4/2023 Huh ......................... B23K 9/16 345/8

FOREIGN PATENT DOCUMENTS

EP 3541220 B1 9/2019
KR 101271686 B1 6/2013
KR 1020210035612 A 4/2021

(Continued)

*Primary Examiner* — Woody A Lee, Jr.

(74) *Attorney, Agent, or Firm* — Dinsmore & Shohl LLP; Yongsok Choi, Esq.

(57) ABSTRACT

A welding information providing apparatus is disclosed. The welding information providing apparatus includes a main body worn by a user, a camera unit provided to an outside of the main body and including at least one camera obtaining welding image frames for a welding process, an image generating unit provided to inside the main body and generating a welding image based on the welding image frames, a display unit displaying the welding image provided from the image generating unit toward a user, a processor for controlling the image generating unit to generate the welding image based on the welding image frames, and a power supply unit provided to the main body and supplying a driving power to at least any one of the camera unit, the image generating unit and the processor.

6 Claims, 11 Drawing Sheets

(56) References Cited

FOREIGN PATENT DOCUMENTS

| | | | |
|---|---|---|---|
| KR | 1020210094916 | A | 7/2021 |
| KR | 1020210150156 | A | 12/2021 |
| WO | 2017117675 | A1 | 7/2017 |
| WO | 2022039357 | A1 | 2/2022 |
| WO | 2022072556 | A1 | 4/2022 |

* cited by examiner

WELDING INFORMATION PROVIDING APPARATUS

CROSS-REFERENCE TO RELATED APPLICATION

This application is based on and claims priority under 35 U.S.C. § 119 to Korean Patent Application No. 10-2022-0057405, filed on May 10, 2022, in the Korean Intellectual Property Office, the disclosure of which is incorporated by reference Here in its entirety.

BACKGROUND

1. Field

The present disclosure relates to a welding information providing apparatus.

2. Description of the Related Art

Protective equipment such as a welding mask are used for protecting a user from light and high heat generated in a welding process. Once the user wears the protective equipment, the user only check the welding processes through the protective equipment, and thus, the user has to take off the protective equipment and check with the naked eyes in order to identify various information for the welding operation, such as operation conditions set in a welding apparatus.

When a skill level of an user is not high, and especially, the user wears an automatic welding mask or a manual welding mask, the user may see only some areas adjacent to welding light, and has difficulties in recognizing a specific welding situation, such as the surrounding environments of the welding. Accordingly, there has been a need for providing a high-quality image that allows the user to visually check the surrounding environments of the welding, and for providing the user with specific information on welding state information.

Moreover, the illuminance level/brightness of a welding light spot is very high in the welding operation, a darkening filter is usually used in the welding mask to protect eyes of the user from the welding light spot and to smoothly perform the welding operation. In such a case, nothing other than the welding light spot is visible at all, which makes the welding process very difficult and deteriorates welding accuracy of the welding operation.

In addition, the issues described above usually occurs in medical staffs when performing skin treatment and/or diagnosis by using high bright/high illuminant light such as a laser beam, and also occurs in any other situations when performing some processes using the high bright/high illuminant light.

SUMMARY

The disclosure provides a welding information providing apparatus for improving the user's work conveniences by providing a battery without a wire connected to a separate power source.

However, the tasks to be solved by the disclosure are exemplarily, and are not limited to the issues described above.

Additional aspects will be set forth in part in the description which follows and, in part, will be apparent from the description, or may be learned by practice of the presented embodiments of the disclosure.

According to an aspect of the present disclosure, there is provided a welding information providing apparatus including a main body worn by a user, a camera unit provided to an outside of the main body and including at least one camera obtaining welding image frames for a welding process, an image generating unit provided to inside the main body and generating a welding image based on the welding image frames, a display unit displaying the welding image provided from the image generating unit toward a user, a processor for controlling the image generating unit to generate the welding image based on the welding image frames, and a power supply unit provided to the main body and supplying a driving power to at least any one of the camera unit, the image generating unit and the processor.

In an embodiment, the welding information providing apparatus may further include a path changing unit configured to guide the welding image provided from the image generating unit to the display unit.

In an embodiment, the welding information providing apparatus may further include a fixing unit provided to a side of the main body and fixing the main body to a user's head.

In an embodiment, the fixing unit may include at least one fixing band having a length enough to enclose at least a portion of the use's head.

In an embodiment, the welding information providing apparatus may further include a power supply unit provided to the fixing unit.

In an embodiment, the power supply unit may include at least one battery, and the battery may include a secondary battery.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
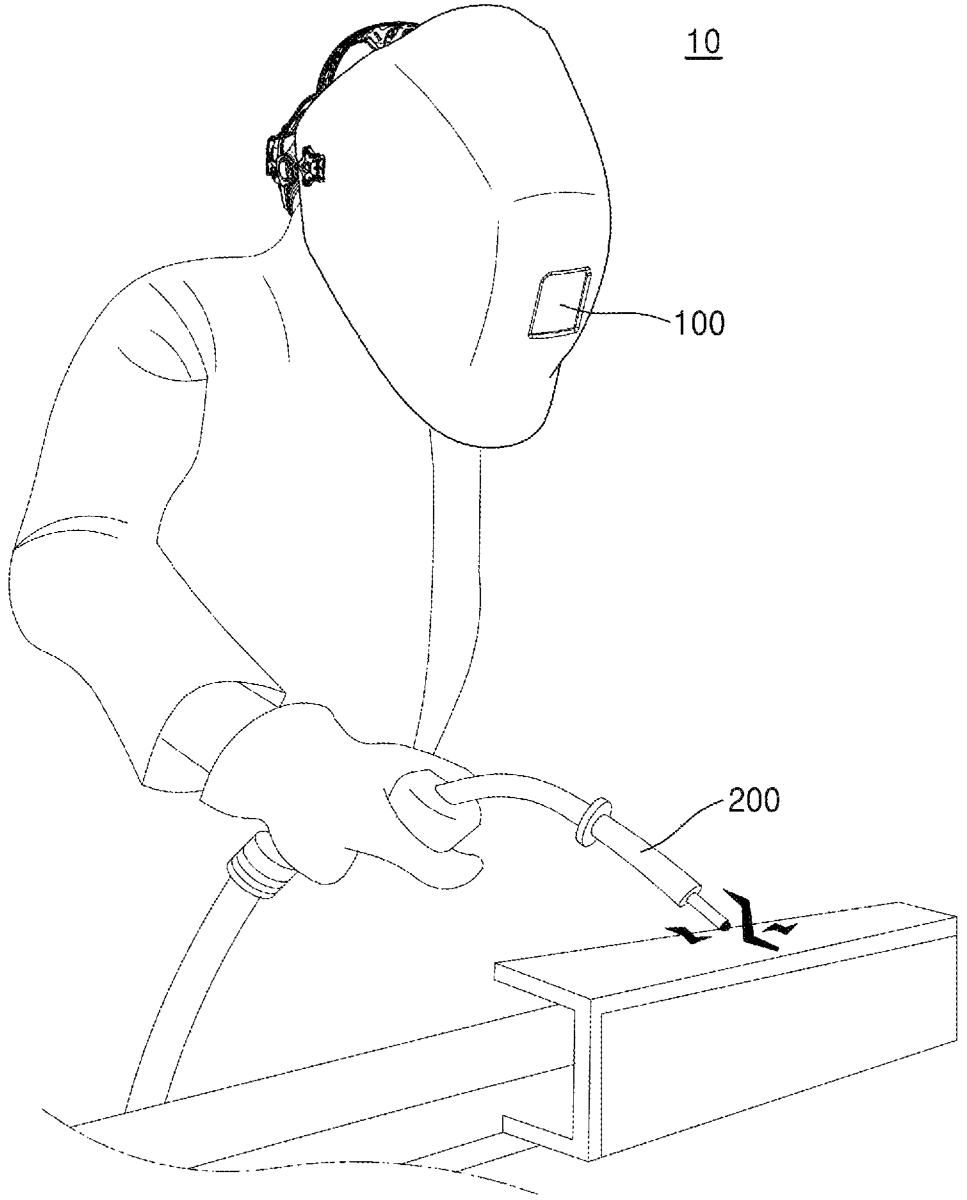
FIG. 1 is a view illustrating a structure of a welding system, according to an embodiment.

Reference will now be made in detail to embodiments, examples of which are illustrated in the accompanying drawings, where like reference numerals refer to like elements throughout. In this regard, the present embodiments may have different forms and should not be construed as being limited to the descriptions set forth herein. Accordingly, the embodiments are merely described below, by referring to the figures, to explain aspects. As used here, the term "and/or" includes any and all combinations of one or more of the associated listed items. Expressions such as "at least one of," when preceding a list of elements, modify the entire list of elements and do not modify the individual elements of the list.

Since the present disclosure can apply various conversions and have various embodiments, specific embodiments will be described in detail by illustrating them in the drawings. Effects and features of the present disclosure and methods of achieving the same will be apparent with reference to embodiments described in detail with reference to the drawings. However, the present invention is not limited to the embodiments disclosed below, but may be implemented in various forms.

Hereafter, embodiments of the present disclosure will be described in detail with reference to the accompanying drawings, and when the same or corresponding elements are described with reference to the drawings, the same reference numerals are assigned and repeated descriptions thereof are omitted.

In the following embodiments, terms, such as "first", "second", and the like, are not used in a limited sense, but are used for the purpose of distinguishing one element from another element.

In the following embodiment, the singular expression includes the plural expression unless it has an explicitly different meaning in the context.

In the following embodiments, the term "include" or "have" means that a feature or an element described in the specification exists, and the possibility of adding one or more other features or elements is not excluded in advance.

In the drawings, the size of elements may be exaggerated or reduced for convenience of description. For example, since the sizes and thicknesses of each element in the drawings are arbitrarily shown for convenience of description, the present invention is not limited to those illustrated.

In the following embodiments, the x-axis, the y-axis, and the z-axis are not limited to three axes on the Cartesian coordinate system, and may be interpreted in a broad meaning including the same. For example, the x-axis, the y-axis, and the z-axis may be orthogonal to each other, but may refer to different directions that are not orthogonal to each other.

When an embodiment may be implemented differently, a specific process order may be performed differently from the order described. For example, two processes described in succession may be performed substantially simultaneously or may be performed in the opposite order to the order described.

Hereafter, the welding information providing apparatus 100 according to an embodiment is described in detail on the basis of the above-mentioned principle.

FIG. 1 is a view illustrating a structure of a welding system, according to an embodiment.

Referring to FIG. 1, a welding system 10 according to an embodiment may include a welding information providing apparatus 100 and a welding torch 200. The welding information providing apparatus 100 and the welding torch 200 may be connected to each other through a communication network to transmit and receive data. The welding information providing apparatus 100 and the welding torch 200 may operate in a one-to-one match, but are not limited thereto and may operate in a one-to-n correspondence. That is, n welding torches 200 may be connected to a single welding information providing apparatus 100, or a single welding torch 200 may be connected to n welding information providing apparatuses 100. In addition, the welding information providing apparatus 100 and the welding torch 200 may exchange data by communicating with an additional server (not shown).

The welding information providing apparatus 100 may provide information on a welding situation to a user. In detail, the welding information providing apparatus 100 may obtain a welding image by using at least one camera module included in a camera unit of the welding information providing apparatus 100, generate a composite image based on the welding image, and display the composite image to the user. The welding information providing apparatus 100 may generate the composite image by using a high dynamic range (HDR) technology, and may display a high-definition composite image to the user. Thus, the user may visually check information on a shape of welding beads and a surrounding environment except for the areas adjacent to the welding light by the high-definition composite image.

The welding information providing apparatus 100 according to an embodiment may obtain the welding image from the camera unit at a position equal to the user's field of view. Accordingly, the welding information providing apparatus 100 according to an embodiment may obtain the welding image similar to an image that is obtained when the user directly looks at a work site, thereby providing more accurate welding information to the user.

In addition, the welding information providing apparatus 100 according to an embodiment may compose and provide a high-definition welding image by an image composition, and to this end, a plurality of images may be obtained by two or more camera modules and each image may be displayed on at least a display unit. For example, the camera unit may include two cameras which may be arranged at positions respectively corresponding to left and right eyes of the user.

The welding information providing apparatus 100 may obtain a plurality of images by repeatedly taking pictures with different shutter speeds, ISO sensitivities, and gain values of each camera, and may composite the plurality of images. The welding information providing apparatus 100 according to an embodiment may improve the image quality by the contrast ratio treatment on the obtained composite image.

In addition, the welding information providing apparatus 100 may provide a function of displaying welding information in preferred color (for example, green and blue) by using a RGB (red, green, blue) filter. In addition, The welding information providing apparatus 100 according to an embodiment may provide a function of correcting power of a magnifying glass (for example, screen enlargement and reduction). In addition, the welding information providing apparatus 100 according to an embodiment may provide a temperature composite image by using an additional thermal imaging camera. Thus, the welding information providing apparatus 100 may indicate a welding temperature in a color. The welding information providing apparatus 100 according to an embodiment may support a function of providing sound (for example, guidance alarm) or guidance voice for all the functions described above.

The welding torch 200 according to an embodiment may detect a welding situation including a welding temperature, a welding direction, a welding inclination, a welding speed, a distance between a base material and the welding torch, etc. from at least a sensor in a real-time when performing the welding operation. The welding torch 200 may monitor the state of the torch and change the operation setting value of the torch according to the welding situation.

The welding information providing apparatus 100 according to an embodiment may receive information on the operation setting and the operation state from the welding torch 200 through a communication network connected to the welding torch 200, and may provide the user with operation information based on the received welding information through visual feedback.

For example, upon receiving sensing information on a welding temperature value, the welding information providing apparatus 100 may generate a notification corresponding to the temperature value in various ways such as light, vibration, or a message etc. Here, the notification may be visual feedback provided to the display unit of the welding information providing apparatus 100, and may be auditory feedback through sound (for example, guidance alarm) or guidance voice.

In addition, the sensing information on the temperature value may include information on whether or not the temperature value exceeds a preset temperature range. Also, the sensing information about the temperature value may include a numerical value, a grade, a level, etc. corresponding to an actual temperature on a welding surface.

When the temperature of the torch and the welding surface exceeds the preset temperature range, the welding information providing apparatus 100 according to an embodiment may guide the user to stop the welding operation. In the case of welding out of the preset temperature range, there is a risk of quality deterioration, and thus the user may be guided to adjust the temperature of the torch.

Here, the visual feedback may be to provide an icon indicating danger on a partial area of the display unit of the welding information providing apparatus 100 displaying the work site. In another embodiment, the welding information providing apparatus 100 may provide welding stop guidance through visual feedback by repeating increasing and decreasing the saturation of a specific color (for example, red) on the entire screen of the display unit.

The welding information providing apparatus 100 according to an embodiment may detect welding information from a sensor in the welding information providing apparatus 100 as well as at least a sensor in the welding torch 200. Here, the welding information including the welding situation, for example, a degree of light related to the real-time welding operation, a welding temperature, a welding direction, a welding inclination, a welding speed, a distance between the base material and the welding torch, etc. may be detected from at least a sensor.

Likewise, the welding information providing apparatus 100 may provide guidance corresponding to the welding information based on the welding information detected from the sensor (for example, first sensor) in the welding information providing apparatus 100.

According to an embodiment, the welding information providing apparatus 100 may change the operation of the welding torch 200 by sensing a preset user movement or a preset user voice after the welding stop guidance is provided.

In another embodiment, when in poor communication with the welding torch 200, the welding information providing apparatus 100 may obtain temperatures of the torch and the welding surface by an image sensor provided there. For example, the welding information providing apparatus 100 may obtain temperature values of the torch and the welding surface based on image data obtained from a thermal imaging camera.

Although the above-described embodiment discloses that the information received from the welding torch 200 is only welding temperature information, the welding information providing apparatus 100 may provide any other guidance for various welding information, as would be known to one of ordinary skill in the art.

Figure 2:
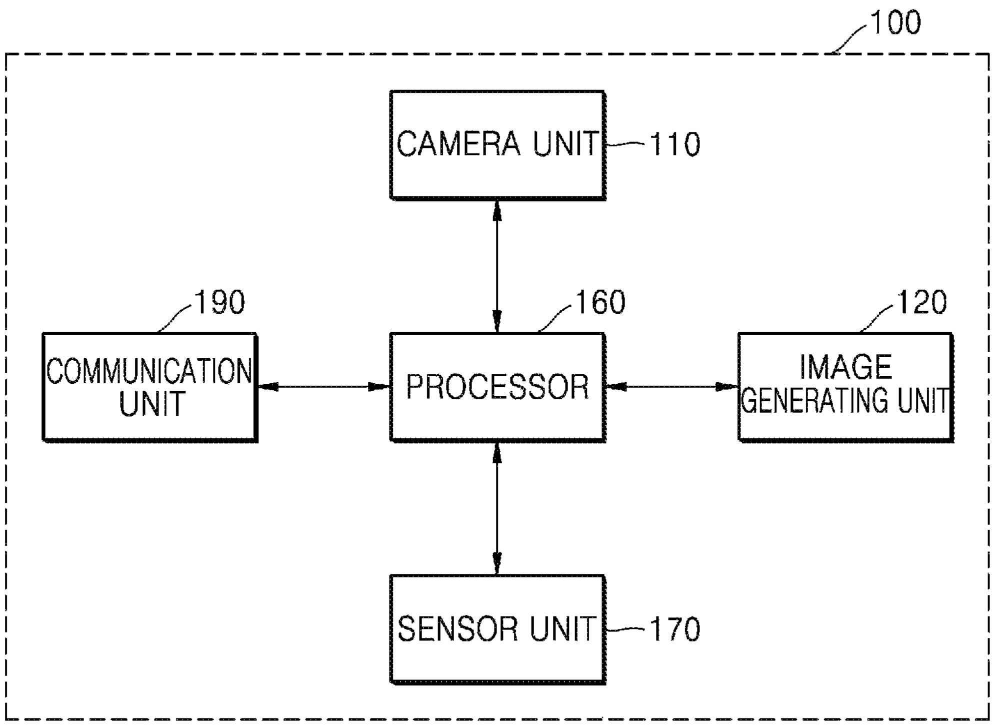
FIG. 2 is a schematic block diagram for describing elements of the welding information providing apparatus according to an embodiment.
Figure 3:
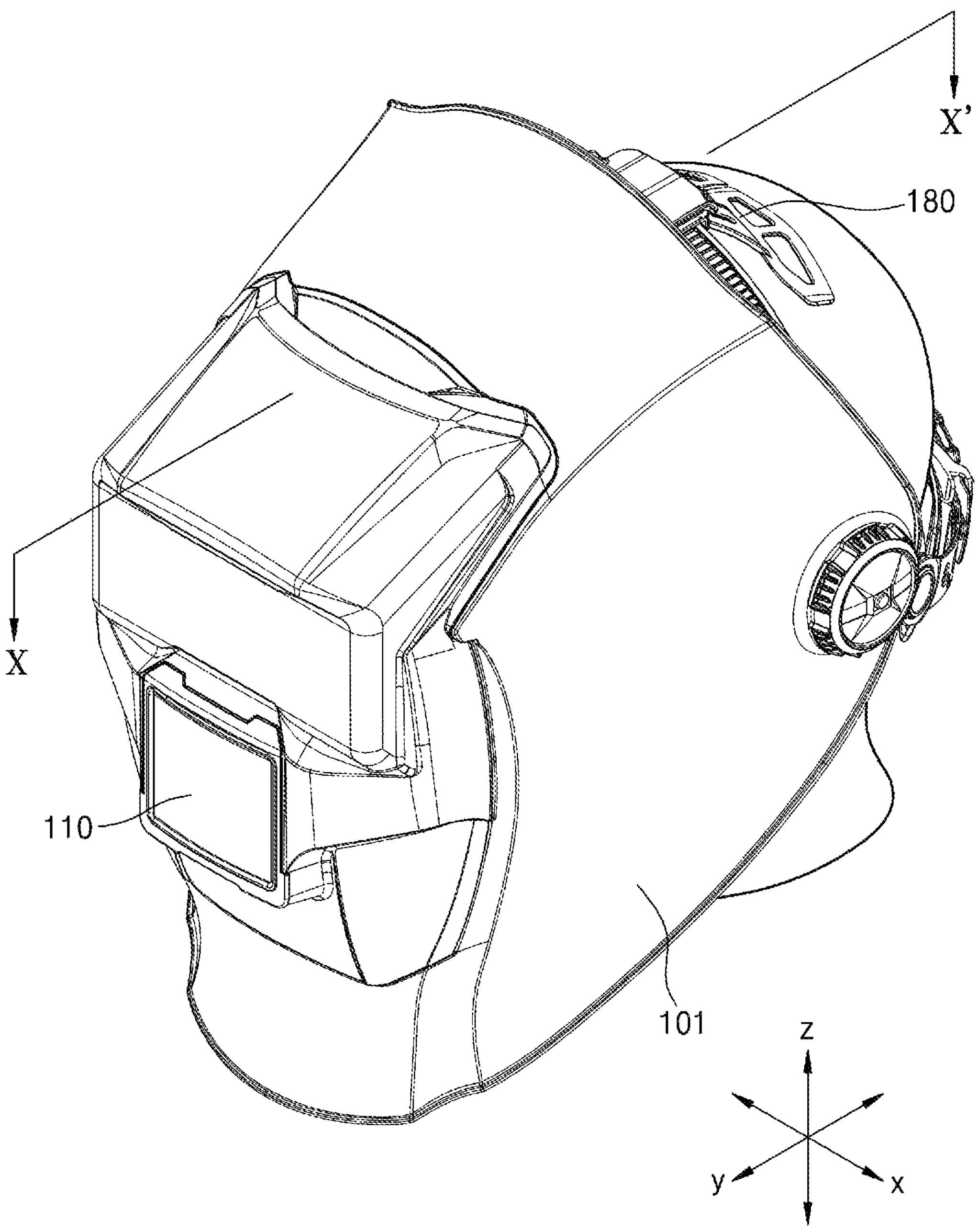
FIG. 3 is a perspective view illustrating a welding information providing apparatus according to an embodiment.
Figure 4:
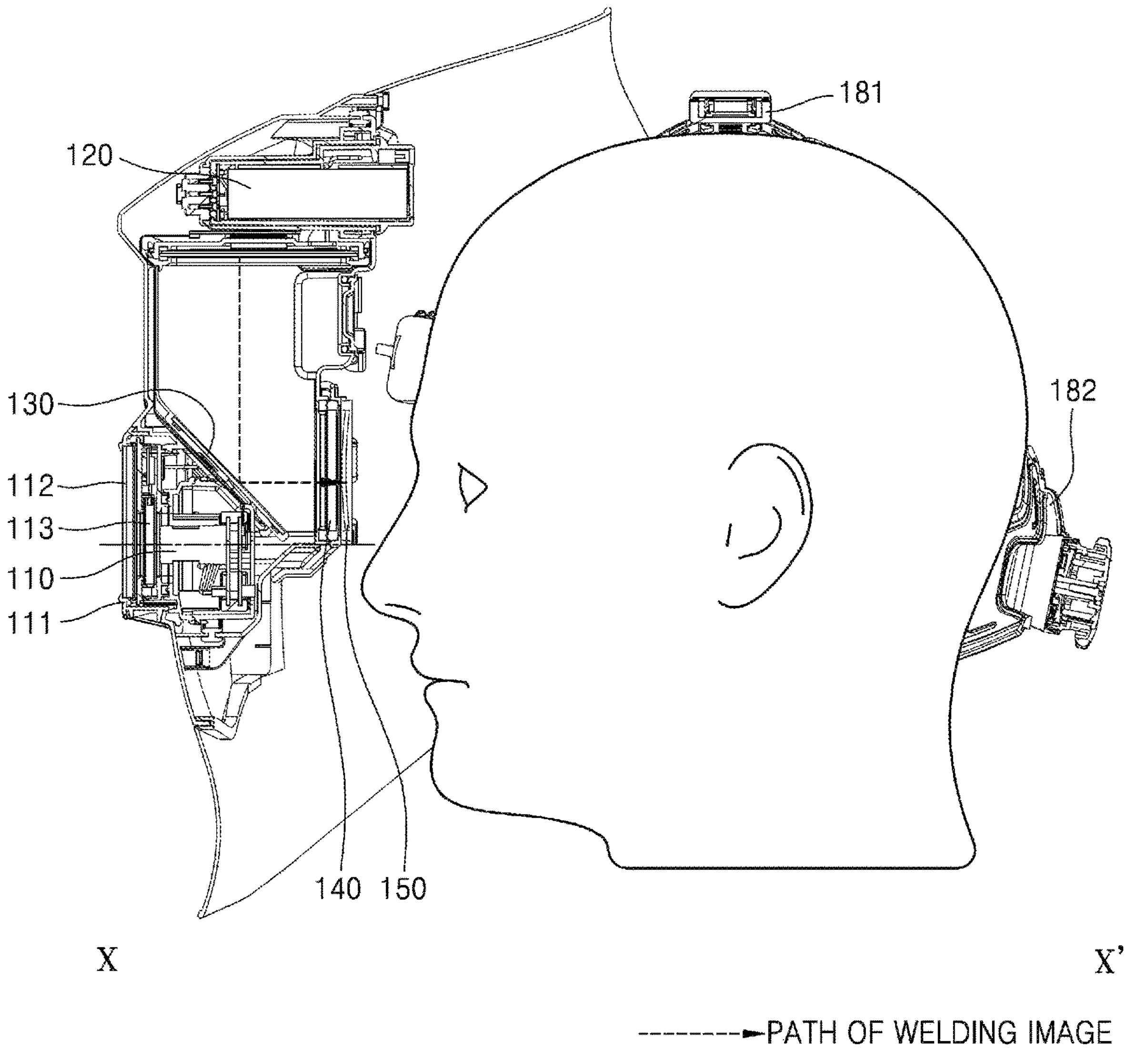
FIG. 4 is a cross-sectional view taken along line III-III' of FIG. 3.

FIG. 2 is a schematic block diagram for describing elements of the welding information providing apparatus according to an embodiment, FIG. 3 is a perspective view illustrating a welding information providing apparatus according to an embodiment, and FIG. 4 is a cross-sectional view taken along line III-III' of FIG. 3.

Referring to FIGS. 2 to 4, the welding information providing apparatus 100 according to an embodiment may constitute the welding system 10 together with the welding torch 200. In an embodiment the welding information providing apparatus 100 may include a main body 101, a camera unit 110, an image generating unit 120, a path changing unit 130, a display unit 140, a lens unit 150, a processor 160, a sensor unit 170, and a communication unit 190. In addition, the welding information providing apparatus 100 may include a fixing unit 180 positioned on a rear surface of the main body 101 to fix the welding information providing apparatus 100 to the user's head.

The main body 101 may be provided to be worn by the user for protecting the user's face. The main body 101 may be formed of a material having a certain strength, for example, reinforced plastic, but the material of the main body 101 is not limited to the reinforced plastic, so that various materials may be used for the main body 101, as long as the materials are sufficiently resistant to elements such as sparks that are unexpectedly occur in the welding process.

The main body 101 may be fixed to the user's head by the fixing unit 180 provided inside the main body 101. The fixing unit 180 may have a structure including a plurality of ribs, such as a headgear, and an element including a soft material such as a fiber material or a cushion material may be arranged on at least a portion of an inner surface of the fixing unit 180 that is in direct contact with the user's head.

The camera unit 110 may include at least one camera mounted on the outside of the main body 101 and acquiring a welding image frame for the welding.

The camera unit 110 may receive a control command from the processor 160 and change camera settings such as a shutter speed, an ISO sensitivity, and a gain in response to the control command, and then may take pictures of various phenomena in the welding process.

In an embodiment, the camera unit 110 may be located on the front of the main body 101 corresponding to the user's field of view. The camera unit 110 may include a camera to obtain the welding image frame of the welding, but the present disclosure is not limited thereto.

In another embodiment, the camera unit 110 may include a pair of cameras located at positions corresponding to the user's left and right eyes, respectively. In another embodiment, the camera unit 110 may further include a camera that obtains the welding image frame by taking a picture from a location other than the front portion of the main body 101 corresponding to the user's field of view.

The camera unit 110 may include an outer cover to protect the camera. The outer cover may include an outer cover frame 111, an outer cover plate 112 and a light blocking cartridge 113.

The outer cover frame 111 may perform a function of coupling the camera unit 110 to the main body 101.

The outer cover plate 112 may be positioned in front of the light blocking cartridge 113 to protect the light blocking cartridge 113. The outer cover plate 112 may include a material through which light may pass, for example, a transparent material. The outer cover plate 112 may include a resin, such as polycarbonate and acrylic, and may be formed by an injection molding.

The light blocking cartridge 113 may block welding light generated in the welding process. That is, the light blocking cartridge 113 may be blackened based on welding light information detected from the sensor unit 170, for example, a photosensor, to thereby increase the light blocking degree of the cartridge. Particularly, the light blocking cartridge 113 may include, for example, a liquid crystal display panel (LCD panel) capable of adjusting the degree of blackening according to the alignment direction of liquid crystals. For example, the light blocking cartridge 113 may be implemented with various panels such as a vertical align (VA) type LCD panel, a twist nematic (TN) type LCD panel, and an in-plane switching (IPS) type LCD panel.

The degree of blackening of the light blocking cartridge 113 may be automatically controlled according to the brightness of the welding light. As described above, when the degree of blackening is automatically controlled according to the brightness of the welding light, the sensor unit 170 may be used for detecting the brightness of the welding light. For example, the sensor unit 170 may detect the light intensity of the welding light to obtain welding light information and transmit the information on the intensity of the welding light included in the welding light information to the processor 160 to be described later as a preset electrical signal, and the processor 160 may control the degree of blackening based on the intensity of the welding light.

That is, the light blocking cartridge 113 may change the light blocking degree of the panel in real time to deal with the intensity of welding light generated on the welding surface of the welding site, and the camera unit 110 may take the welding image under circumstances that some of the welding light is shielded by the light blocking cartridge 113 provided in front of the camera unit 110.

In another embodiment, no light blocking cartridge 113 may be provided with the welding information providing apparatus 100. In this case, the user may perform the welding only with the welding image from the camera unit 110.

The camera unit 110 according to an embodiment may include a thermal imaging camera. The welding information providing apparatus 100 may obtain a temperature image by composing a thermal image obtained by the thermal imaging camera with an image of the welding site.

In an embodiment, a lighting unit (not shown) may be further provided with the welding information providing apparatus 100 in such a configuration that the lighting unit is electrically connected to the processor 160. The lighting unit (not shown) may be positioned at an outside of the welding information providing apparatus 100 and be configured to radiate light toward at least an area of the welding site. The lighting unit (not shown) may include a plurality of LED modules, and an output level of light irradiated by the lighting unit (not shown) may be controlled by the processor 160. In an embodiment, the lighting unit (not shown) may operate in link with the operation of the camera unit 110 under the control of the processor 160.

The image generating unit 120 may be positioned at an inside of the main body 101 and generate the welding image based on the welding image frame obtained by the camera unit 110. Then, the image generating unit 120 may provide the welding image to the user. The image generating unit 120 may provide the original welding image obtained from the camera unit 110 as it is or the high-definition composite image including the welding information.

For example, the image generating unit 120 may provide the high-definition composite image in such a way that the user can visually check the surrounding environment (for example, the shape of a pre-worked welding bead, etc.) other than the area adjacent to the welding light. In addition, the image generating unit 120 may provide the visual feedback (for example, a welding direction) on the welding state to the user, to thereby guide the welding process.

The image generating unit 120 may include a display panel for generating image light including welding image information and an optical system for diffusing the image light from the display panel. The image generating unit 120 may include a projector for generating and projecting the welding image by the display panel and the optical system.

The display panel of the image generating unit 120 may generate and emit the image light including the welding image information. The display panel may include a liquid crystal display (LCD) panel, an organic light emitting diodes (OLED) panel, a light-emitting diodes (LEDs) panel, and a liquid crystal on silicon (LCoS) panel, but the display panel is not limited to the panels described above.

The image generating unit 120 may be located in the main body 101 in such a position that the welding image is indirectly provided to the user's field of view by the path changing unit 130 instead of being directly provided.

In an embodiment, the image generating unit 120 may be located in such a position that the welding image is provided in a direction perpendicular to the optical axis AX1 of the camera unit 110. That is, as illustrated in FIG. 4, the image generating unit 120 may be positioned near the user's forehead and may provide the welding image to the path changing unit 130.

The path changing unit 130 may change the path of the welding image provided from the image generating unit 120 and guide the welding image toward the eyes of the user. For example, the path changing unit 130 may include a mirror, an X-cube prism, a dichroic filter, and the like, for reflecting the welding image.

Accordingly, the welding information providing apparatus 100 may be configured to be small in size. For example, as illustrated in FIG. 4, the image generating unit 120 may be located at various positions, such as adjacent area of the user's forehead, thus, the size of the welding information providing apparatus 100 may be reduced. That is, the welding information providing apparatus may have a limitation that the size cannot increase more than a prerequisite size due to the characteristics of performing the welding under circumstances that the user directly wears the welding information providing apparatus 100, however, the limitation may be overcome by the present embodiment of the present disclosure.

Although the present embodiment discloses that the path changing unit 130 includes one mirror as illustrated in the drawings, the technical concept of the present disclosure is not limited thereto, and the path changing unit 130 may include more mirrors and/or any other members for changing the path of the welding image, as would be known to one of ordinary skill in the art.

A welding image whose path has been changed by the path changing unit 130 may be provided to the display unit 140.

The display unit 140 may include a means for displaying the welding image, which is provided by the image generating unit 120, to the user. That is, the display unit 140 may transmit a high-definition composite image of the welding process, to thereby provide the composite image to the user.

The display unit 140 may be located at a position corresponding to the user's eyes in such a configuration that the display unit 140 may be located between the path changing unit 130 and the user's eyes, so that the welding image is provided to the user by transmitting therethrough. The display unit 140 may be positioned closer to the lens unit 150, which is described later, than to the path changing unit 130.

In an embodiment, a single display unit 140 may be provided with the welding information providing apparatus 100. For example, the user may detect the welding image by simultaneously looking at the single display unit 140 with both eyes.

In another embodiment, a pair of the display units 140 may be provided with the welding information providing apparatus 100. For example, a pair of the display units 140 may be arranged in correspondence to the user's left and right eyes, respectively, and each display unit 140 may provide welding images to the user's left and right eyes, respectively.

The display unit 140 may include, for example, a rear projection screen. The welding image may be projected on a rear surface of the screen from the image generating unit 120 via the path changing unit 130, and be displayed on a front surface of the screen. A welding image displayed on the front surface of the screen may be provided to both eyes of the user. However, the display unit 140 is not limited to the rear projection screen, and may include any other displays that are implemented with various display technologies, as long as the other displays provide the welding image to the user from the image generating unit 120.

The welding information providing apparatus 100 may include a lens unit 150 for focusing the welding image to both eyes of the user from the display unit 140 in a short distance. The welding information providing apparatus 100 according to an embodiment may provide the welding image by displaying on the display unit 140 spaced apart from a user's eyes by a predetermined distance. However, since the human eye has difficulties in focusing on an object that is too close, the lens unit 150 may be further positioned between the display unit 140 and the user's eyes for controlling the focal length between the user's eyes and the welding image on the display unit 140.

That is, the lens unit 150 be positioned on a path through which the welding image transmitted from the display unit 140 passes, and may adjust the size of the welding image, to thereby provide the adjusted welding image to both eyes of the user. The arrangement of the lens unit 150 between the display unit 140 and the user's eyes may reduce the gap distance between the user's eyes and the display unit 140, and thus the size of the welding information providing apparatus 100 may also be compactly reduced. Accordingly, the user may ensure a wide field of view and a clear image even in the enclosed space within the welding information providing apparatus 100.

For example, the distance between the display unit 140 and the lens unit 150 may be shorter than the focal length of the lens unit 150. In addition, the lens unit 150 may project the welding image transmitted through the display unit 140 in front of the user as a virtual image. Thus, the user may feel as if the welding image were farther than the distance of the actual display unit 140, and may obtain the effect of looking at the welding image on the display unit 140 as an enlarged virtual image with a wide viewing angle.

The lens unit 150 may include a glass material, a plastic material, and the like, and the plastic material may include various transparent resins, such as (meth)acrylic resin, styrene resin, and polycarbonate resin. In addition, each lens of the lens unit 150 may be coated with a filter that blocks light of a specific wavelength band. For example, the lens unit 150 may include a lens coated with a filter for blocking blue light.

The processor 160 may compose welding image frames, which are received from the camera unit 110, to thereby generate the high-definition composite image. The processor 160 may obtain a composite image by setting different photographing conditions for each frame of the camera unit 110 and composing the frames acquired in time-serial order in parallel. In detail, the processor 160 may control the camera unit 110 to take pictures by changing the shutter speed, ISO sensitivity, and gain of the camera unit 110.

Here, the processor 160 may differently set the photographing conditions according to conditions such as the sensed welding light at the welding site, ambient light, and the motion degree of the welding torch 200. Specifically, the processor 160 may set the photographing conditions in such a way that the ISO sensitivity and the gain decrease as the welding light and/or ambient light of the welding site increases. In addition, the processor 160 may also set the photographing conditions in such a way that the shutter speed increases as the movement of the welding torch 200 and/or the work speed of the welding are/is detected to be fast.

The processor 160 may compose images of a preset number of frames in parallel. In an embodiment, each image of the preset frames may be taken under different photographing conditions.

When two or more cameras are provided with the camera unit 110, the processor 160 according to an embodiment may control each camera to take images under different photographing conditions. In this case, the processor 160 may compose images of a preset number of frames in parallel.

In addition, the processor 160 may control the image generating unit 120 to generate the welding image based on the welding image frame obtained from the camera unit 110. Here, the processor 160 may control image settings, such as a size, a brightness, and a contrast of the welding image provided to the user.

The processor 160 may control overall operations of the welding information providing apparatus 100 using various programs stored in a memory (not shown). For example, the processor 160 may include a CPU, a random access memory (RAM) device, a read only memory (ROM) device, and a system bus. Here, various instruction sets for booting the system may be stored in the ROM device, and the CPU may copy an operating system (O/S) to the RAM device from the memory of the welding information providing apparatus 100 in which the operating system (O/S) is stored according to the instructions stored in the ROM device and may execute the O/S to boot the system. When the system booting is completed, the CPU may copy various applications stored in the memory to the RAM device and execute the applications, to thereby perform various operations. Although the present embodiment discloses that the processor 160 includes only one CPU, the processor 160 may be implemented with a plurality of CPUs (or DSPs, SoCs, etc.), as would be known to one of ordinary skill in the art.

In an embodiment, the processor 160 may include a digital signal processor (DSP) for processing digital signals, a microprocessor, and/or a time controller (TCON). However, the processor 160 is not limited to the DSP, the microprocessor, and the time controller described above, and may include at least one of a central processing unit (CPU), a micro controller unit (MCU), a micro processing unit (MPU), a controller, an application processor (AP), a communication processor (CP), and an ARM processor or may be defined in the above terms. In addition, the processor 160 may be implemented as a system on chip (SoC), a large scale integration (LSI) chip having a built-in processing algorithm, or in the form of a field programmable gate array (FPGA).

The sensor unit 170 may include a plurality of sensor modules configured to detect various types of information around the welding site and obtain the welding information. Here, the welding information may include a welding temperature, a welding direction, a welding inclination, a welding speed, a distance between a base material and the welding torch, etc. that are detected in a real-time in the welding process. Furthermore, the sensor unit 170 may include an optical sensor module configured to detect a light level at least within the welding area.

According to an embodiment, the sensor unit 170 may include an illuminance sensor, and thus, the sensor unit 170 may obtain information on the intensity of welding light at the welding site. The sensor unit 170 may further include various types of sensors such as a proximity sensor, a noise sensor, a video sensor, an ultrasonic sensor, and an radio frequency (RF) sensor as well as the illuminance sensor, and may detect various changes related to the welding environment.

The communication unit 190 may be an element for receiving welding information from the welding torch 200 and transmitting commands for controlling the welding torch 200. In an embodiment, the communication unit 190 may transmit the composite image to an external device other than the welding torch 200. Here, the external device may include various devices including a communication module, such as a smart phone of a user/a third party, a computer, etc.

The communication unit 190 may include a component for performing communication with various types of external devices according to various types of communication methods. The communication unit 190 may include at least one of a wireless fidelity (Wi-Fi) chip, a Bluetooth® chip, a wireless communication chip, and a near field communication (NFC) chip. In particular, when the communication unit 190 uses the Wi-Fi chip or the Bluetooth® chip, various connection information, such as an subsystem identification (SSID) and a session key, may be firstly transmitted to and/or received from the communication unit 190, and then various information may be transmitted to and/or received from the communication unit 190 after the communication between the Wi-Fi chip or the Bluetooth® chip and the communication unit 190 is established using the connection information. The wireless communication chip includes a chip that performs communication according to various communication standards such as IEEE, Zigbee, 3rd Generation (3G), 3rd generation partnership project (3GPP), and long term evolution (LTE). The NFC chip may include a chip that operates in a near field communication (NFC) process with a frequency of about 13.56 MHz among various RF-ID frequency bands such as about 135 kHz, about 13.56 MHz, about 433 MHz, about 860 to about 960 MHz, and about 2.45 GHz.

In addition, the welding torch 200 may include an additional communication unit, sensor unit, and second processor.

The communication unit transmits and receives data with the welding information providing apparatus 100. The communication unit may include a communication module for a short-range wireless communication (for example, Bluetooth®, wifi, wifi-direct), a long-distance wireless communication (3G, High-Speed Downlink Packet Access (HSDPA)), and a long term evolution (LTE).

The sensor unit or the second sensor may be included in the welding torch and may detect the welding situation, such as a welding temperature, a welding speed, a welding inclination, a welding direction, and a distance between the base material and the welding torch.

The sensor unit may detect at least one of various changes, such as a posture change of the user holding the welding torch 200, an illumination change of the welding surface, and an acceleration change of the welding torch 200, and may transfer electrical signals corresponding to the detected changes to the second processor. That is, the sensor unit may detect the state change made based on the welding torch, generate a detection signal corresponding to the state change, and transfer the detection signal to the second processor.

The sensor unit may include various sensors, and an electrical power may be supplied to at least one of the sensors under the control when the welding torch 200 is driven or under the user setting-based control, to thereby detect the state change of the welding torch 200.

In this case, the sensor unit may be configured to include at least one of all types of sensing devices for detecting the state change of the welding torch 200. For example, the sensor unit may include at least one of various sensing devices, such as an acceleration sensor, a gyro sensor, an illuminance sensor, a proximity sensor, a pressure sensor, a noise sensor, a video sensor, a gravity sensor, etc. The light degree of the welding area detected by the illuminance sensor of the welding torch 200 may be transmitted to the processor 160 by the communication unit, and the processor 160 may control the lighting unit (not shown) and/or the camera unit 110 based on the light degree transmitted from the illuminance sensor of the welding torch 200 instead of the sensor unit 170 of the welding information providing apparatus 100.

The acceleration sensor may be an element for detecting the movement of the welding torch 200. In detail, since the acceleration sensor may detect dynamic forces such as an acceleration force, a vibration force, and an impact of the welding torch 200, the movement of the welding torch 200 may be sufficiently detected by the acceleration sensor.

The gravity sensor may be an element for detecting a direction toward which the gravity works. That is, the detection result of the gravity sensor may be used to determine the movement of the welding torch 200 together with the acceleration sensor. In addition, a grip direction toward which the welding torch 200 is gripped may be determined by the gravity sensor.

In addition to the type of sensor described above, the welding torch 200 may further include various types of sensors, such as a gyroscope sensor, a geomagnetic sensor, an ultrasonic sensor, and an RF sensor, and may detect various changes related to the welding environment.

Figure 5:
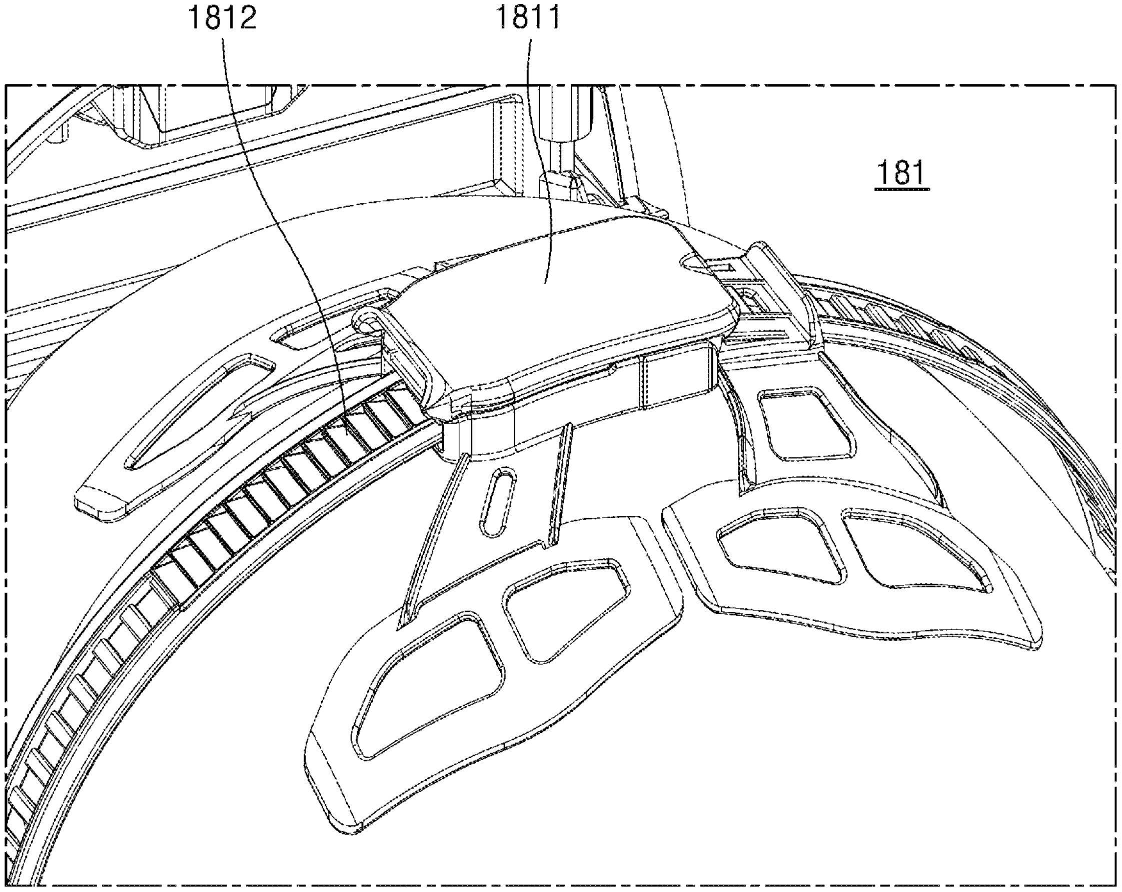
FIG. 5 is a perspective view illustrating a first fixer of the fixing unit shown in FIG. 4.
Figure 6:
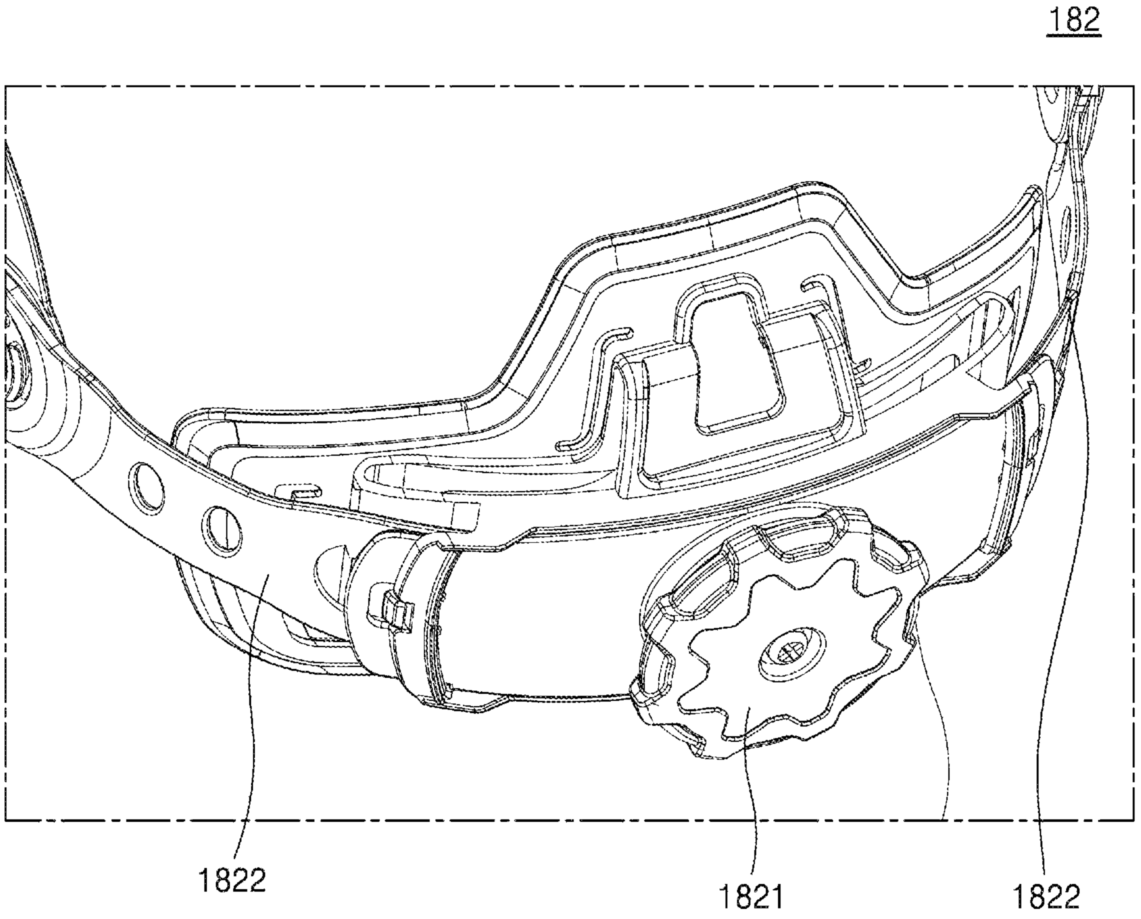
FIG. 6 is a perspective view illustrating a second fixer of the fixing unit shown in FIG. 4.
Figure 7:
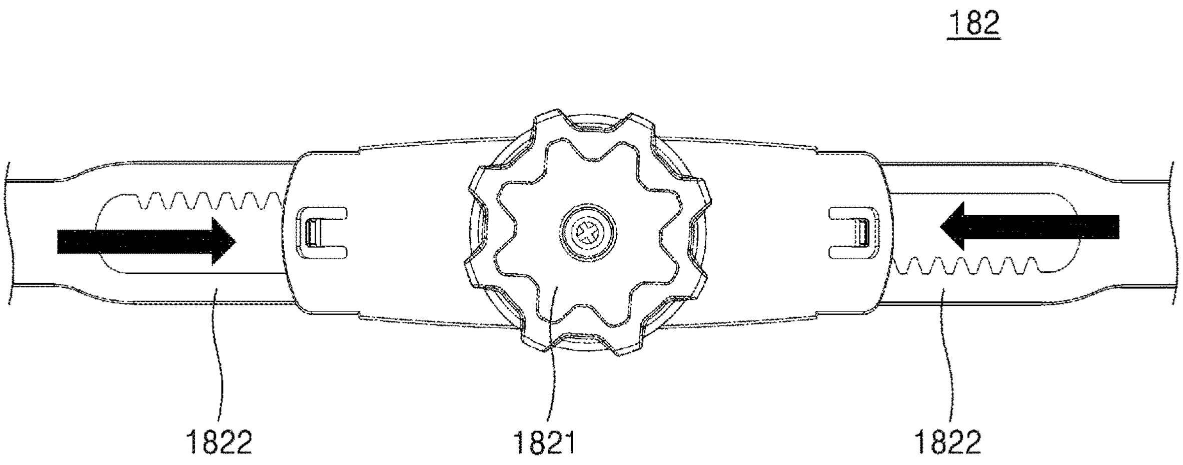
FIG. 7 is a view illustrating a driving state of the second fixer 182 shown in FIG. 6.

FIG. 5 is a perspective view illustrating a first fixer 181 of the fixing unit 180 shown in FIG. 4, and FIG. 6 is a perspective view illustrating a second fixer 182 of the fixing unit 180 shown in FIG. 4. FIG. 7 is a view illustrating a driving state of the second fixer 182 shown in FIG. 6.

Referring to FIGS. 5 to 7, the fixing unit 180 may be provided on the main body 101. For example, the fixing unit 180 may be positioned on at least a side of the main body 101. The fixing unit 180 may enclose at least a portion of the user's head. For example, the fixing unit 180 may include at least one fixing band having a length enough to enclose at least a portion of the user's head.

In an embodiment, the fixing unit 180 may include a plurality of fixers. For example, the fixing unit 180 may include at least one of a first fixer 181, which is positioned on an upper side of the user's head, and a second fixer 182, which is positioned on the back side of the user's head.

Referring again to FIG. 5, the first fixer 181 may be positioned at the upper portion of the user's head. For example, the first fixer 181 may include a first fastener 1811 and a first fixing band 1812 inserted into the first fastener 1811 and having a length enough to enclose at least a portion of the user's head.

In an embodiment, a plurality of hook teeth may be provided on the surface of the first fixing band 1812. In addition, a plurality of locking jaws may be provided at an inside the first fastener 1811. Therefore, the user may adjust the length of the first fixing band 1812 by pushing the first fixing band 1812 into the first fastener 1811 after wearing the main body 101.

In detail, the locking jaw may have a protrusion and a pair of the neighboring hook teeth may have such slopes that the locking jaw is well inserted forward between the neighboring hook teeth and is hard to separate backward from the neighboring hook teeth, so that the locking jaw is allowed to move forward and is prevented from moving backward by the slopes of the hook teeth. Accordingly, when the user pushes the first fixing band 1812 into the first fastener 1811, the locking teeth may pass through the locking teeth, but the user may not move the first fixing band 1812 in the reverse direction.

In addition, the first fastener 1811 may further include a separator for separating the locking jaw from the hook teeth. For example, the locking jaw may be separated from the hook teeth by a user's manipulation of the separator, and the first fixing band 1812 may be released from the first fastener 1811.

Accordingly, the user can adjust the length of the first fixing band 1812 suitable for the size of the user's head.

Referring again to FIGS. 6 and 7, the second fixer 182 may be positioned on the back of the user's head. For example, the second fixer 182 may include a second fastener 1821 and a second fixing band 1822 inserted into the second fastener 1821 and having a length to enclose at least a rear portion of the user's head.

In an embodiment, a plurality of hook teeth may be provided on the surface of the second fixing band 1822. In addition, a plurality of locking jaws may be provided at an inside the second fastener 1821.

The second fastener 1821 may be driven in a rotational manner. For example, the second fastener 1821 may include a rotating member which is interlocked with the locking jaw in the second fastener 1821, so that the locking jaw may move according as the user rotates the rotating member. In this case, since the locking jaw is engaged with the hook teeth of the second fixing band 1822, when the user rotates the rotating member, the second fixing band 1822 may be inserted into the second fastener 1821 forward or withdrawn from the second fastener 1821 backward.

Accordingly, the user may easily adjust the length of the second fixer 182. For example, the user may easily adjust the welding information providing apparatus 100 suitable for the size of the user's head just by manipulating the rotating member even when the user holds the welding torch in one hand.

Figure 8:
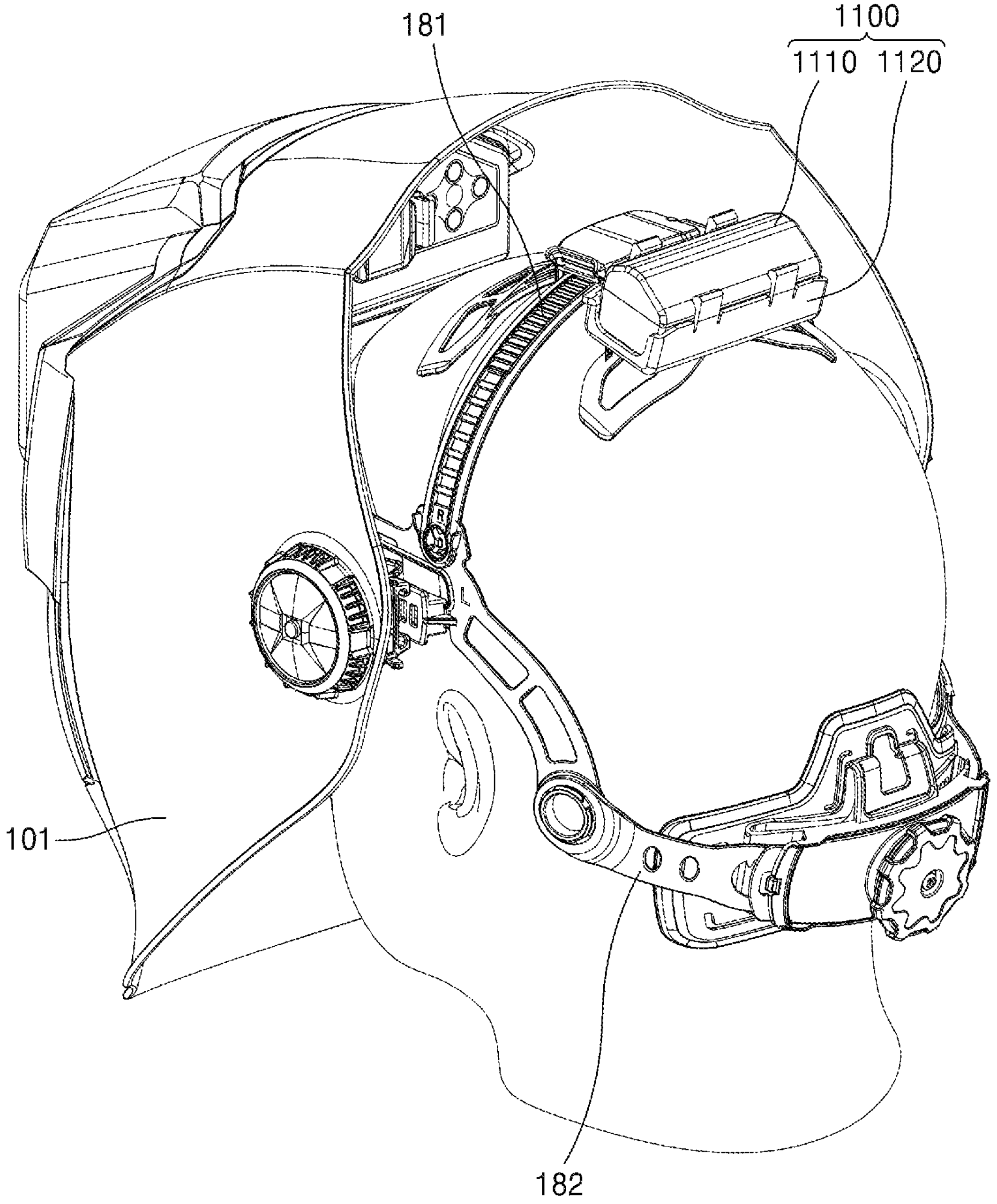
FIG. 8 is a perspective view illustrating a welding information providing apparatus including a power supply unit, according to an embodiment.

FIG. 8 is a perspective view illustrating a welding information providing apparatus 100 including a power supply unit 1100, according to an embodiment.

Referring to FIG. 8, the welding information providing apparatus 100 according to an embodiment may further include a power supply unit 1100.

The power supply unit 1100 may be provided to the main body 101.

The power supply unit 1100 may supply driving power to at least one of the camera unit 110, the image generating unit 120, the processor 160, the sensor unit 170, and the communication unit 190.

In an embodiment, the power supply unit 1100 may include a battery 1110. For example, the battery 1110 may supply the driving power to various elements of the welding information providing apparatus 100.

In an embodiment, the battery 1110 may include a secondary battery. Thus, the battery 1110 may be charged.

For example, the user may charge the battery 1110 when not using the welding information providing apparatus 100. Thereafter, when the user starts the welding process together with the welding information providing apparatus 100, the charging of the battery 1110 may be stopped and the battery 1110 may supply the driving power to the welding information providing apparatus 100, to thereby work the welding information providing apparatus 100 in the welding process.

In an embodiment, the battery 1110 may include any one of a nickel battery, an ion battery, a lithium ion battery, a lithium polymer battery, a lithium sulfa battery, and a polymer battery. However, various electric storage members are provided with the power supply unit 1100 as long as the electric charge and discharge are repeated.

The driving power may be used at least one of the camera unit 110, the image generating unit 120, the processor 160, the sensor unit 170, and the communication unit 190 comprising the welding information providing apparatus 100. Therefore, the conventional welding information providing apparatus may be usually used in a wired connection with an external power source. However, due to the characteristics of the welding site, wearing the wired welding information providing apparatus 100 and performing the welding process causes a lot of inconveniences to a user.

However, the welding information providing apparatus 100 according to an embodiment may eliminate the inconveniences by using the power supply unit 1100. That is, since the power supply unit 1100 provided to the main body 101 supplies the driving power to each element of the welding information providing apparatus 100, the external power source and the connecting wire may not be needed. Therefore, when the welding information providing apparatus 100 is not in use, the user may make the battery 1110 of the power supply unit 1100 to charge, and when the welding information providing apparatus 100 is in use, the user wearing the welding information providing apparatus 100 may perform the welding process without any wires connected to the external power source.

Referring again to FIG. 8, the power supply unit 1100 may be provided on the first fixer 181.

The power supply unit 1100 may include the battery 1110 and a battery holder 1120.

As described above, the battery 1110 may supply the driving power to each element of the welding information providing apparatus 100. The battery 1110 may be seated in the battery holder 1120. For example, the battery 1110 may be inserted into the battery holder 1120 and the battery holder 1120 may be connected to the first fixer 181.

A space for receiving the battery 1110 may be provided in the battery holder 1120. In an embodiment, the battery 1110 may be detachably seated in the space of the battery holder 1120. For example, the battery 1110 may be separated from the battery holder 1120, and thus the separated battery 1110 may be individually charged apart from the battery holder 1120, and then the charged battery 1110 may be inserted into the battery holder 1120, so that the driving power may be supplied to the welding information providing apparatus 100 from the charged battery 1110.

In detail, the power supply unit 1100 may be provided to the first fastener 1811. Therefore, even when the first fixing band 1812 is inserted into the first fastener 1811 or separated from the first fastener 1811, the power supply unit 1100 may remain fixed in the original position.

Figure 9:
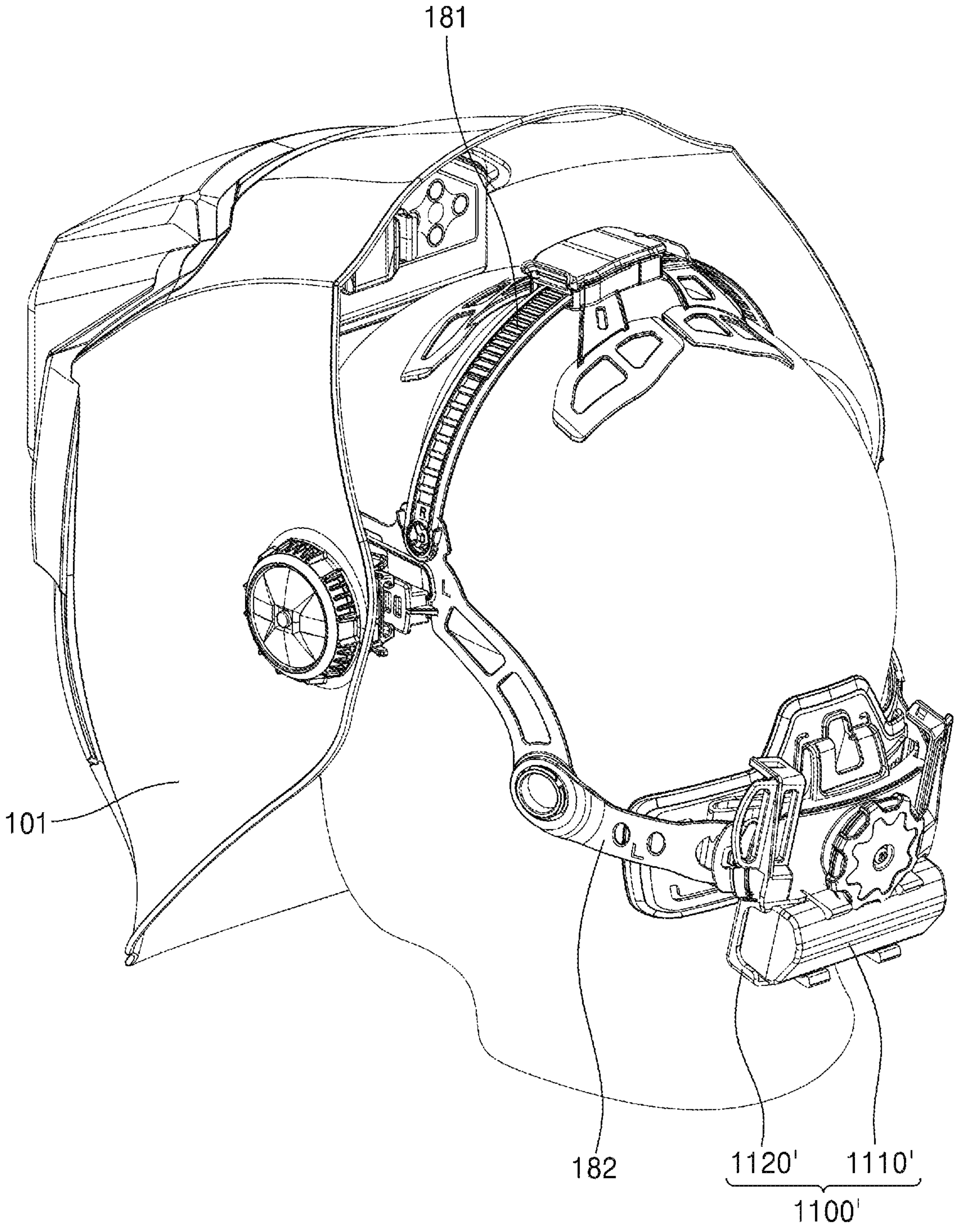
FIG. 9 is a perspective view illustrating a welding information providing apparatus including another power supply unit, according to another embodiment.

FIG. 9 is a perspective view illustrating a welding information providing apparatus 100 including another power supply unit 1100', according to another embodiment.

For conveniences, the same descriptions as the embodiments given above will be omitted or briefly given.

The welding information providing apparatus 100 according to another embodiment may further include a first modified power supply unit 1100'. Here, the first modified power supply unit 1100' may be provided to the main body 101, for example, to the second fixer 182.

The first modified power supply unit 1100' may include a first modified battery 1110' and a first modified battery holder 1120'.

Like the battery 1110, the first modified battery 1110' may supply the driving power to each element of the welding information providing apparatus 100. The first modified battery 1110' may be seated on the first modified battery holder 1120'. For example, the first modified battery 1110' may be inserted into the first modified battery holder 1120', and the first modified battery holder 1120' may be connected to the second fixer 182.

A space for holding the first modified battery 1110' may be provided in the first modified battery holder 1120'. In an embodiment, the first modified battery 1110' may be detachably provided in the space of the first modified battery holder 1120'. For example, the first modified battery 1110' may be separated from the first modified battery holder 1120', and thus the separated first modified battery 1110' may be individually charged apart from the first modified battery holder 1120', and then the first charged modified battery 1110' may be inserted into the first modified battery holder 1120', so that the driving power may be supplied to the welding information providing apparatus 100 from the first charged modified battery 1110'.

In detail, the first modified power supply unit 1100' may be provided to the second fastener 1821. Therefore, even when the second fixing band 1822 is inserted into the second fastener 1821 or separated from the second fastener 1821, the first modified power supply unit 1100' may remain fixed in the original position.

Figure 10:
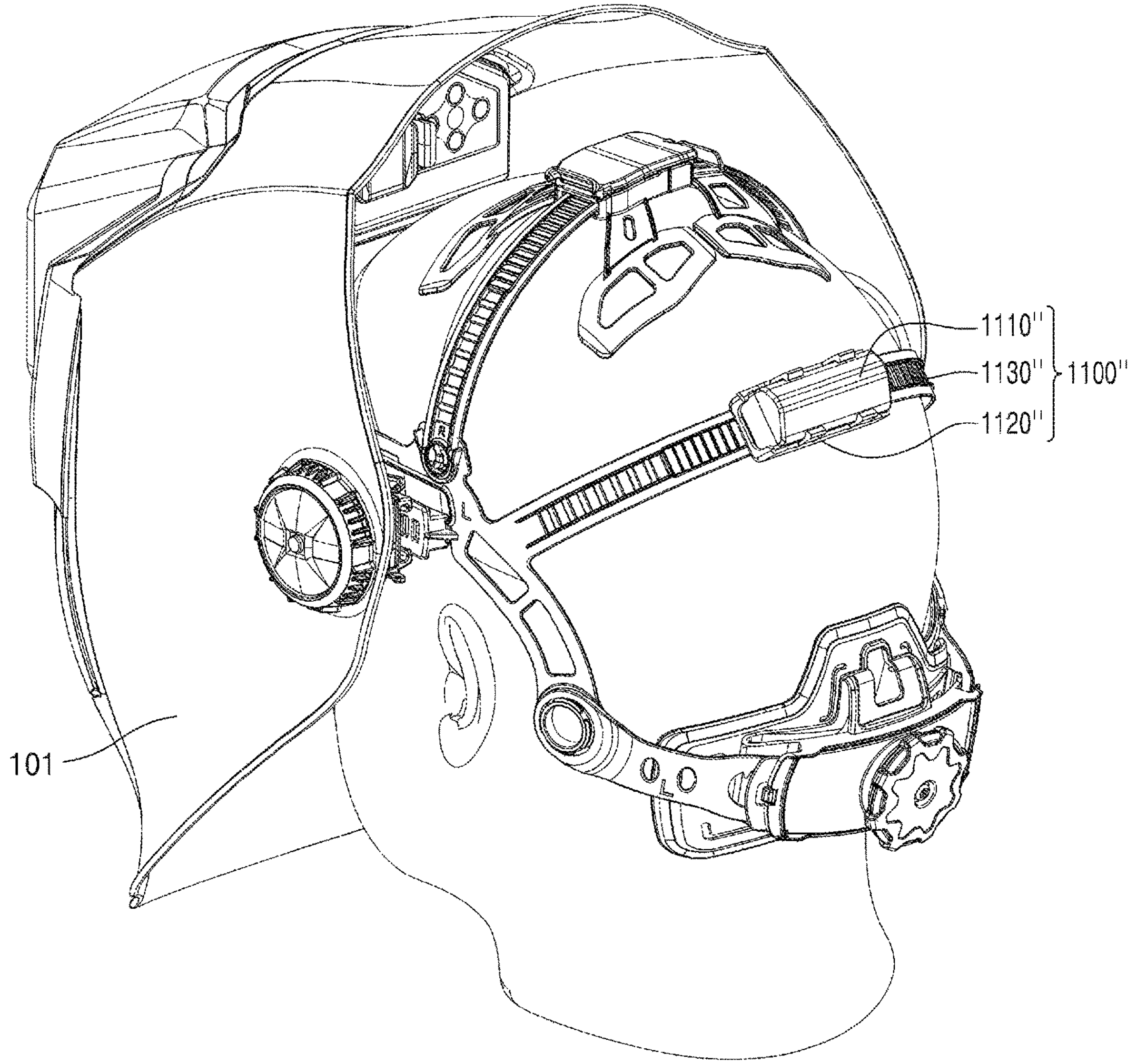
FIG. 10 is a perspective view illustrating a welding information providing apparatus including another power supply unit, according to another embodiment.

FIG. 10 is a perspective view illustrating a welding information providing apparatus 100 including another power supply unit 1100", according to another embodiment.

For conveniences, the same descriptions as the embodiments given above will be omitted or briefly given.

The welding information providing apparatus 100 according to another embodiment may further include a second modified power supply unit 1100". Here, the second modified power supply unit 1100" may be provided to the main body 101, for example, to a third fixing band 1130" connected to the second modified power supply unit 1100".

The second modified power supply unit 1100" may include a second modified battery 1110" and a second modified battery holder 1120".

Like the battery 1100, the second modified battery 1110" may supply the driving power to each element of the welding information providing apparatus 100. The second modified battery 1100" may be seated on the second modified battery holder 1120". For example, the second modified battery 1110" may be inserted into the second modified battery holder 1120", and the second modified battery holder 1120" may be connected to the third fixing band 1130".

A space for holding the second modified battery 1110" may be provided in the second modified battery holder 1120". In an embodiment, the second modified battery 1110" may be detachably provided in the space of the second modified battery holder 1120". For example, the second modified battery 1110" may be separated from the second modified battery holder 1120", and thus the separated second modified battery 1110" may be individually charged apart from the second modified battery holder 1120", and then the second charged modified battery 1110" may be inserted into the second modified battery holder 1120", so that the driving power may be supplied to the welding information providing apparatus 100 from the second charged modified battery 1110".

In detail, the second modified power supply unit 1100" may be provided to the third fixing band 1130". That is, the main body 101 may further include the third fixing band 1130" for providing the second modified power supply unit 1100", and the second modified power supply unit 1100" may be stably fixed to the main body 101 by connecting the second modified to the third fixing band 1130", so that the second modified power supply unit 1100" may be supported by the user's head when the user wears the welding information providing device 100.

Figure 11:
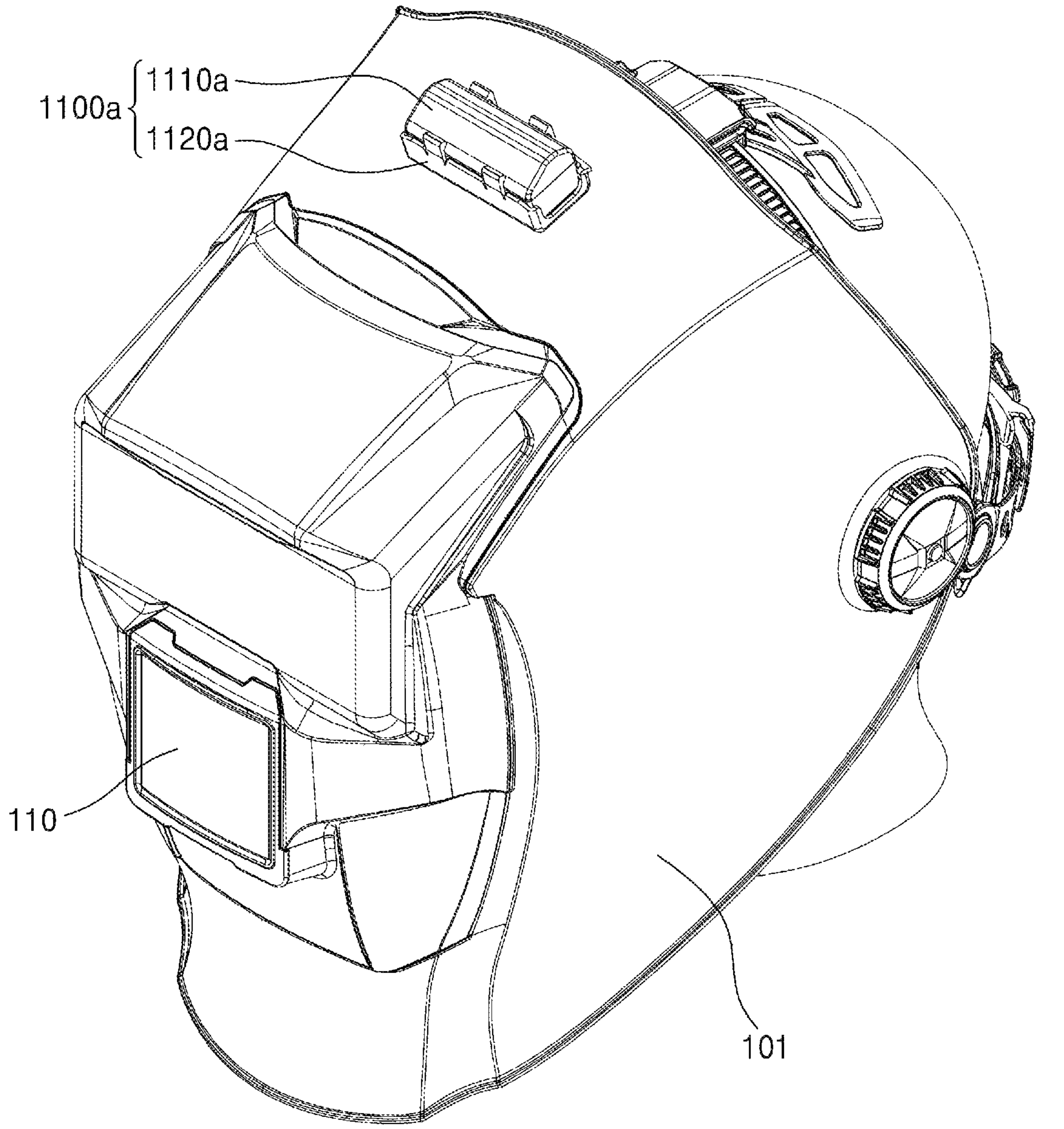
FIG. 11 is a perspective view illustrating a welding information providing apparatus including another power supply unit, according to another embodiment.

FIG. 11 is a perspective view illustrating a welding information providing apparatus 100 including another power supply unit **1100*a***, according to another embodiment.

For conveniences, the same descriptions as the embodiments given above will be omitted or briefly given.

The welding information providing apparatus 100 according to another embodiment may further include a third modified power supply unit **1100*a*. Here, the third modified power supply unit 1100*a* may be provided to the main body 101, for example, onto a surface of the main body 101**.

The third modified power supply unit **1100*a* may include a third modified battery 1110*a* and a third modified battery holder 1120*a***.

Like the battery 1100, the third modified battery **1110*a* may supply the driving power to each element of the welding information providing apparatus 100. The third modified battery 1100*a* may be seated on the third modified battery holder 1120*a*. For example, the third modified battery 1110*a* may be inserted into the third modified battery holder 1120*a*, and the third modified battery holder 1120*a* may be fixed onto the surface of the main body 101**.

A space for holding the third modified battery **1110*a* may be provided in the third modified battery holder 1120*a*. In an embodiment, the third modified battery 1110*a* may be detachably provided in the space of the third modified battery holder 1120*a*. For example, the third modified battery 1110***a* may be separated from the third modified battery holder 1120*a*, and thus the separated third modified battery 1110*a* may be individually charged apart from the third modified battery holder 1120*a*, and then the charged third modified battery 1110*a* may be inserted into the third modified battery holder 1120*a*, so that the driving power may be supplied to the welding information providing apparatus 100 from the charged third modified battery 1110*a*.

Although the third modified power supply unit 1100*a* is illustrated to be positioned on an upper outer surface of the main body 101 in FIG. 11, the position of the third modified power supply unit 1100*a* is not limited to the upper outer surface of the main body 101, and thus the third modified power supply unit 1100*a* may be positioned on any other surfaces of the main body 101, such as a side surface, a front surface, or a lower outer surface of the main body 101. In an embodiment, the third modified power supply unit 1100*a* may be fixed to an inner surface of the main body 101.

As described above, the present disclosure has been described with reference to embodiments shown in the drawings, but this is merely exemplary, and those of ordinary skill in the art will understand that various modifications and variations of the embodiments are possible therefrom. Therefore, the true technical protection scope of the present disclosure should be determined by the technical idea of the appended claims.

Specific executions described in the embodiments are examples, and do not limit the scope of the embodiments in any way. For the sake of simplicity of the specification, descriptions on conventional electronic configurations, control systems, software, and other functional aspects of the systems may be omitted. In addition, the connection of lines or connecting members between the elements shown in the drawings represent functional connections and/or physical or circuit connections by way of example, and in actual devices, various functional connections that are replaceable or additional, physical connection, or circuit connections. In addition, if there is no specific reference such as “essential” or “important”, it may not necessarily be an element necessary for the application of the present disclosure.

In the specification of the embodiments (particularly in the claims), the use of the term “the” and similar indicating terms may correspond to both singular and plural. In addition, when a range is described in the embodiment, it includes the disclosure to which individual values belonging to the range are applied (if there is no contrary description), and each individual value constituting the range is described in the detailed description. Finally, if there is no explicit description or description on the order of steps of the method according to the embodiment, the steps may be performed in an appropriate order. Examples are not necessarily limited according to the order of description of the steps. In all embodiments, all examples or all exemplary terms (for example, etc.) are used simply to describe the embodiments in detail, and the scope of the embodiments is not limited due to the examples or exemplary terms unless limited by the claims. In addition, those skilled in the art can appreciate that various modifications, combinations and changes can be made according to design conditions and factors within the scope of the appended claims or equivalents thereof.

The present disclosure may provide a welding information providing apparatus for improving the user’s work convenience by providing a battery, to thereby omit a wire connected to an additional power source.

However, this effect is exemplary, and the scope of the effect of the present disclosure is not limited to the effect described above.

It should be understood that embodiments described Here should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A welding information providing apparatus comprising:
a main body configured to be worn by a user;
a camera unit mounted on an outside of the main body and including at least one camera obtaining welding image frames with respect to a welding process;
an image generating unit located in an inside of the main body and generating a welding image based on the welding image frames to provide the same;
a display unit displaying the welding image provided from the image generating unit toward a user;
a processor configured to control the image generating unit to generate the welding image based on the welding image frames;
a power supply unit configured to supply power to at least one of the camera unit, the image generating unit and the processor; and
a fixing unit connected to a side of the main body and configured to fix the main body on a user’s head,
wherein the fixing unit includes at least one fixing band having a length enough to enclose at least a portion of the user’s head, and
wherein the power supply unit includes at least one battery installed in the fixing unit.

2. The welding information providing apparatus of claim 1, further comprising:
a path changing unit configured to guide the welding image provided from the image generating unit to the display unit.

3. The welding information providing apparatus of claim 1, wherein
the battery includes a secondary battery.

4. The welding information providing apparatus of claim 1, wherein the fixing unit further includes a fastener, and the fixing band is inserted into the fastener, and wherein the power supply unit is installed in the fastener when the fixing band is inserted into the fastener or separated from the fastener.

5. The welding information providing apparatus of claim 4, wherein
the fastener is a first fixer configured to be disposed on an upper portion of the user’s head.

6. The welding information providing apparatus of claim 4, wherein the fastener is a second fixer configured to be disposed on a rear portion of the user’s head.

* * * * *